United States Patent [19]

Oren et al.

[11] Patent Number: 5,344,986
[45] Date of Patent: Sep. 6, 1994

[54] AMINO PHENOXY COMPOUNDS AND PROCESS FOR THEIR PREPARATION

[75] Inventors: Jakob Oren, Bialik; Joshua Hermolin, Ramat-Hasharon; David Feldman; Michael Zviely, both of Haifa; Dov Zamir, Ha-Sharon; Hugo Keselman, Karmiel, all of Israel

[73] Assignee: Bromine Compounds, Ltd., Beer-Sheva, Israel

[21] Appl. No.: 665,908

[22] Filed: Mar. 7, 1991

[30] Foreign Application Priority Data

Mar. 8, 1990 [IL] Israel ............................. 93685
Feb. 20, 1991 [IL] Israel ............................. 97301

[51] Int. Cl.$^5$ ............................................. C07C 217/90
[52] U.S. Cl. ................................. 564/430; 564/399; 564/328; 564/330
[58] Field of Search ................ 564/430, 328, 330

[56] References Cited

U.S. PATENT DOCUMENTS

| | | | |
|---|---|---|---|
| 2,765,341 | 10/1956 | Wirth et al. | 260/571 |
| 3,558,703 | 1/1971 | Adam et al. | 260/563 |
| 3,944,575 | 3/1976 | Villaescusa et al. | 260/395 |
| 4,593,056 | 6/1986 | Qureshi et al. | 523/445 |

FOREIGN PATENT DOCUMENTS

| | | |
|---|---|---|
| 0184751 | 12/1984 | European Pat. Off. . |
| 1909520 | 9/1970 | Fed. Rep. of Germany . |
| 2636379 | 3/1977 | Fed. Rep. of Germany . |
| 8607597 | 12/1986 | World Int. Prop. O. . |

OTHER PUBLICATIONS

J. Applied Polymer Science, 28(6), 2069–2081 (1983).
J. Aducci, et al "Synthesis, Characterization".
Patent Abstracts of Japan 11, No. 268, Aug. 29, 1987 (Japan 6270347).
Patent Abstracts of Japan 2, No. 140 Nov. 18, 1978 (Japan 53104695).

Primary Examiner—Allen J. Robinson
Assistant Examiner—Brian M. Burn
Attorney, Agent, or Firm—Michael N. Meller

[57] ABSTRACT

Compounds of the formula:

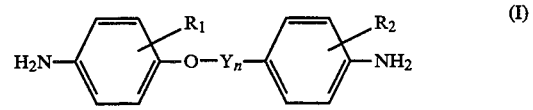

wherein:
n=0 or 1;
$R_1$ and $R_2$ are $C_1$ to $C_3$ alkyl groups, or $R_2$ may be H when n=0; and Y is selected from the group:

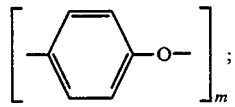

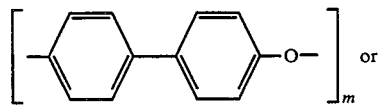

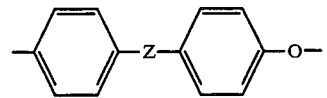

wherein:
m=1–6
Z=$SO_2$, S, C=O, $CH_2$ or $C(CH_3)_2$; and a process for their preparation are described.

2 Claims, 8 Drawing Sheets

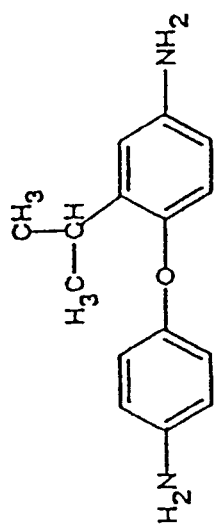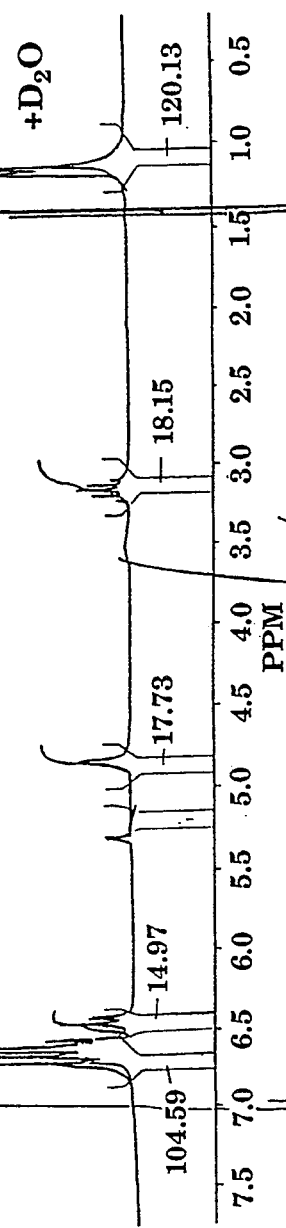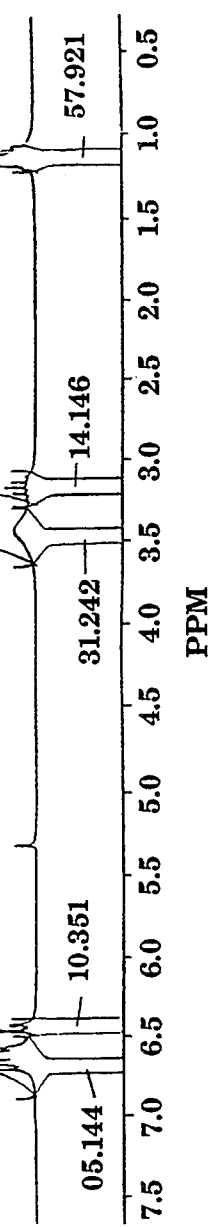
Fig. 6(a)
Fig. 6(b)

AMINO PHENOXY COMPOUNDS AND PROCESS FOR THEIR PREPARATION

FIELD OF THE INVENTION

The present invention relates to novel amino compounds and to a process for the preparation of such compounds.

SUMMARY OF THE INVENTION

The compounds according to the invention have the formula:

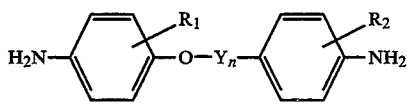
(I)

wherein:
$n = 0$ or 1;
$R_1$ and $R_2$ are $C_1$ to $C_3$ alkyl groups, or $R_2$ may be H when $n=0$; and Y is selected from the group:

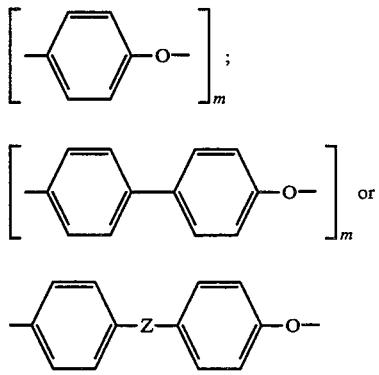

wherein:
$m = 6$;
$Z = SO_2$, S, C=O, $CH_2$ or $C(CH_3)_2$.
and $R_1$ and $R_2$ are each 3-methyl Compounds in which $Z = C(CH_3)_2$ when $Y =$

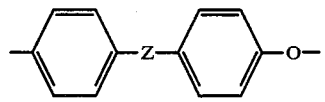

are known in the art and are not claimed herein. Illustrative, but non-limitative, examples of compounds of formula I include:
4,4′-bis (4″-amino-2″-methylphenoxy) diphenylmethane
4,4′-bis (4″-amino-3″-methylphenoxy) diphenylmethane
4,4′-bis (4″-amino-2″-methylphenoxy) diphenyl sulfide
4,4′-bis (4″-amino-3″-methylphenoxy) diphenyl sulfide
2,2-bis [4′-(4″-amino-2″-methylphenoxy)phenyl]propane
4,4′-bis (4″-amino-2″-methylphenoxy) benzophenone
4,4′-bis (4″-amino-3″-methylphenoxy) benzophenone
4,4′-diamino-3-methyl-diphenyl ether
4,4′-diamino-2-isopropyldiphenyl ether
1,4-bis (4′-amino-3′-methylphenoxy) benzene
1,4-bis (4′-amino-2′-methylphenoxy) benzene
4,4′-bis (4″-amino-2″-methylphenoxy) biphenyl
4,4′-bis (4″-amino-3″-methylphenoxy) biphenyl
4,4′-bis (4″-amino-2″-methylphenoxy) diphenyl ether
4,4′-bis (4″-amino-3″-methylphenoxy) diphenyl ether
4,4′-bis (4″-amino-2″-methylphenoxy) diphenylsulfone
4,4′-bis (4″-amino-3″-methylphenoxy) diphenylsulfone The method of preparation that leads to compounds of formula I involves reacting a compound of the formula:

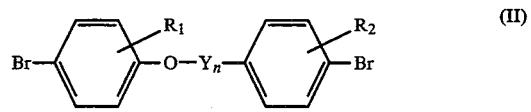
(II)

wherein $R_1$, $R_2$, Y and n have the meanings defined above with respect to the compounds of formula I, with ammonia in aqueous solution at an elevated temperature, in the presence of a copper catalyst.

The preparation of formula I compounds will be illustrated with particular reference to the preparation of 4,4′-diamino-3-methyldiphenylether, as the representative compound. Preparation of further compounds of formula I will be carried out in an analogous manner, as will be further shown hereinafter.

4,4′-Diamino-3-methyl-diphenylether (DAMDPE) is a novel compound, used in the following discussion to represent the compounds of formula I. It is useful, among other things, as a precursor for polymers and for the preparation of further 4,4′-disubstituted-methyl-diphenylethers. These compounds, some of which are also novel and which are described in copending patent applications of the same applicant, include, e.g., 4,4′-diamino-3-methyl-diphenylether-bis-maleimide (DAMDPE-BMI), which is a valuable monomer in the preparation of polymers.

4,4′-Disubstituted phenyl ethers of this type are industrially useful monomers for application in the aviation, electrical, electronics and aerospace industries. Because of the many applications, a wide range of properties are sought by structural changes in the monomers. Thus, altering these monomers by substituents in the aromatic ring, and/or the substitution of one radical which serves to bind two of the aromatic rings by another, affects the softening point, flexibility, heat resistance, etc., of the resins produced therefrom. The improved properties they provide can benefit a wider range of applications which seek better performance from lighter-weight materials. The family of compounds described herein serve to provide this range of variability in the polymer properties.

DAMDPE has the formula:

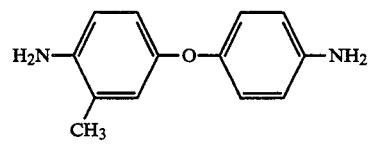

This compound can be prepared by reacting 4,4′-dibromo-3-methyldiphenylether (DBMDPE) with ammonia in aqueous solution and in the presence of a copper catalyst at elevated temperatures. DBMDPE is in itself a novel compound which is described and claimed in a copending patent application of the same applicant.

As said, the reaction which leads to the formation of DAMDPE is an amination reaction of DBMDPE. This reaction is preferably carried out in excess ammonia.

Typically, excesses of ammonia of about 10–15 moles NH3 for each mole of DBMDPE are preferred. Concentrations of about 25% NH3 are suitable, to obtain high time-space yields. To increase the productivity, one may use gaseous NH3 and thereby raise the total amount of the reagents in the reactor.

The reaction can be carried out in a relatively wide range of temperatures, the range of 150°–300° C. being preferred. While different temperatures can be chosen, it will be apparent to the skilled chemist that higher reaction temperatures will result in shorter reaction times, but also in higher pressures, which requires appropriate equipment.

The copper catalyst is a compound of the formula:

$Cu_nR_m$ wherein R is —OH, —O, a halogen or a residue of an organic or an inorganic acid, n is 1 or 2, and m is 0, 1 or 2.

Examples of such copper catalysts are CuO, CuCl, Cu(OAc)$_2$, Cu$_2$O, CuCl$_2$, CuBr$_2$, CuSO$_4$ and CuBr, etc.

BRIEF DESCRIPTION OF THE DRAWINGS

FIGS. 6(a) and 6(b) form the $^1$H-NMR spectrum of DAIPE in CD$_2$Cl$_2$;

Figure 1A:
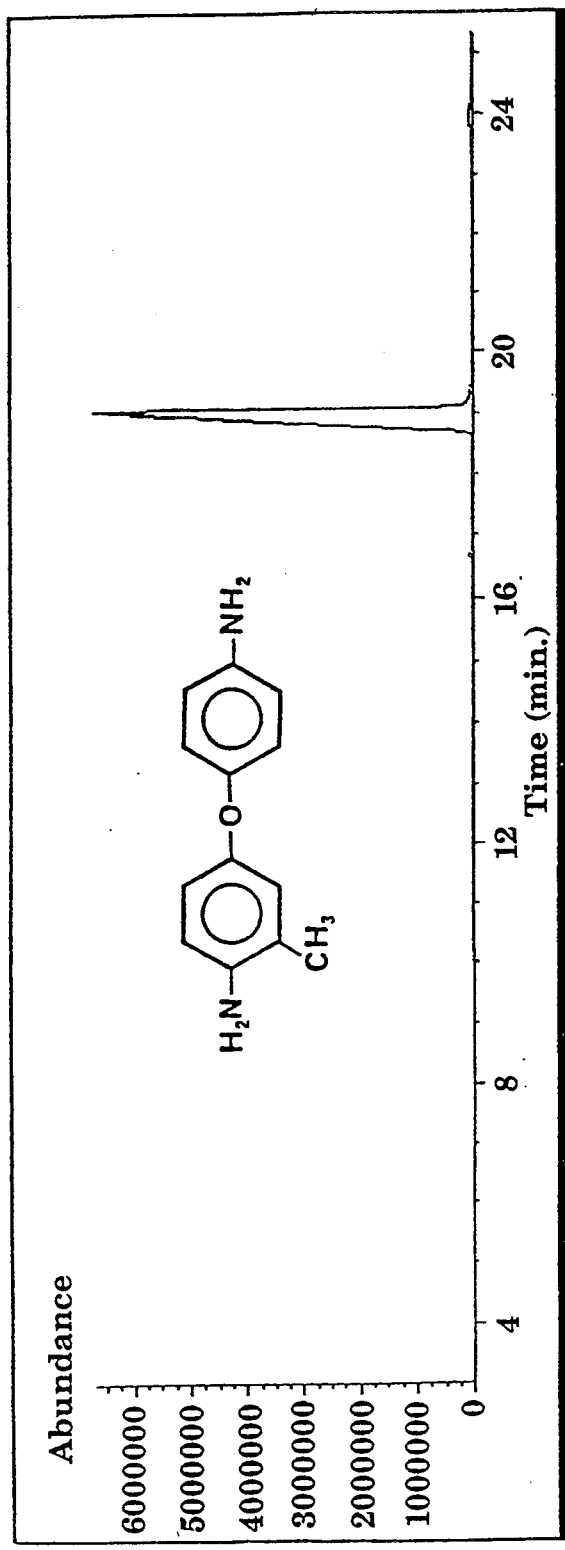
FIGS. 1(a) and 1(b) form the mass spectrum of DAMDPE.

The invention will now be illustrated with reference to the following examples which are not intended to constitute a limitation thereof.

EXAMPLE 1

A.) Preparation of DBMDPE

The starting material, 4,4′-dibromo-3-methyldiphenylether (DBMDPE) was prepared as follows.

To a four-necked round-bottomed flask equipped with a stirrer, a condenser, a dropping funnel and a thermometer, containing a stirred solution of m-phenoxytoluene (m-PHT) (460 g, 2.5 moles) in one liter of dichloromethane, there were added 840 g (5.25 moles) of Br$_2$. The top of the condenser was equipped with a trap to absorb HBr released during the reaction. Br$_2$ was added at a temperature between −5° and 0° C. and in complete darkness, during one hour, and after addition, the reaction mixture was stirred for an additional 1 hour at about 25° C. The progress of the reaction was determined by GC. Excess bromine and traces of HBr were neutralized with aqueous 10% NH3 (150 ml). Two phases formed in the reaction, which were separated, and the organic layer was washed with water (200 ml). After distillation of the solvent in the organic phase, crude DBMDPE (820 g) was obtained, containing 97% of the desired isomer (determined by GC) which represents a yield of 93%.

After crystallization from methanol, a product of 99% purity was obtained, containing 46.4% Br, and having a melting point of 44°–46° C. The crystallization from ethanol gave identical results.

The product so obtained was characterized by GC under the conditions described below, which showed a main peak (99.6%) at a retention time of 7.05 min. The structure of the compound was confirmed by Mass Spectra and NMR, as described in the copending Israeli Patent Application No. 93684 of the same applicant herein, the specification of which is incorporated herein by reference.

B) Preparation of DAMDPE

Into a 1 liter 316 Stainless Steel autoclave, there were added DBMDPE (102.6 g, 0.3 mole), aqueous 25% NH3 (500 ml, 6.5 moles) and Cu SO$_4$·5H$_2$O (100 g, 0.04 mole). The autoclave was sealed and heated to 210° C. under rapid stirring (1000 rpm). The progress of the reaction and its completion were followed by means of a graph of the internal pressure of the autoclave versus time and, at the end of the reaction, by analysis of the Br−. After four hours, the autoclave was cooled to room temperature, the pressure was released, and the autoclave was opened. The reaction mixture was filtered and washed with aqueous 25% NH3 (200 ml) and with water (500 ml).

DAMDPE (58.2 g) was obtained in a purity of 96–98% (determined by qualitative G.C.) and a yield of 88%. After recrystallization from ethyl acetate in the presence of active charcoal, a product of 99% purity was obtained with a m.p. of 153°–155° C. The same result was obtained when recrystallizing from acetonitrile or n-butanol.

The following analysis was obtained:

|  | % H | % N | % C |
| --- | --- | --- | --- |
| Calculated | 6.59 | 13.07 | 72.83 |
| Found | 6.60 | 13.10 | 72.74 |

The analytical data was determined with instruments and conditions as follows:

GC

Gas-chromatograph - Varian 3400

Oven: Initial temperature 100° C., held 1 min., then raised to 250° C. at 15°/min.
Injector: 250° C.
Detector: (transfer line): 300° C.
Column: HP-1 (100% methyl polysiloxane), 5 m ×0.53 mm (megabore)
Injection amounts: 1 μl
Flow: 13 ml/min.
Retention time: 8.1 min.

GC/MS

Gas-chromatograph HP 5890 A

Oven: Initial temperature 100° C., held 1 min. then raised to 240° C. at 15°/min.
Injector: 230° C.
Detector (transfer line): 250° C.
Column SUPELCO (fused silica, capillary column) 30 m ×0.25 mm.
Split ratio: 1:50

Injection amounts: 1 μl
Flow: 0.6 ml/min.
Retention time: 19.1 min.
　Mass Spectrometer HP 5970
Range: 40–550 a.m.n
Scan: every 0.9 second.

| NMR spectra Bruker WP 200 MHz | | |
|---|---|---|
| | $^1$H-NMR | $^{13}$C-NMR |
| Solvent: | DMSO - d$_6$ | DMSO - d$_6$ |
| Scans: | 50 | 10,000 |
| Reference: | TMS | TMS |

IR: FTIR Nicolet 5 MX

Figure 1B:
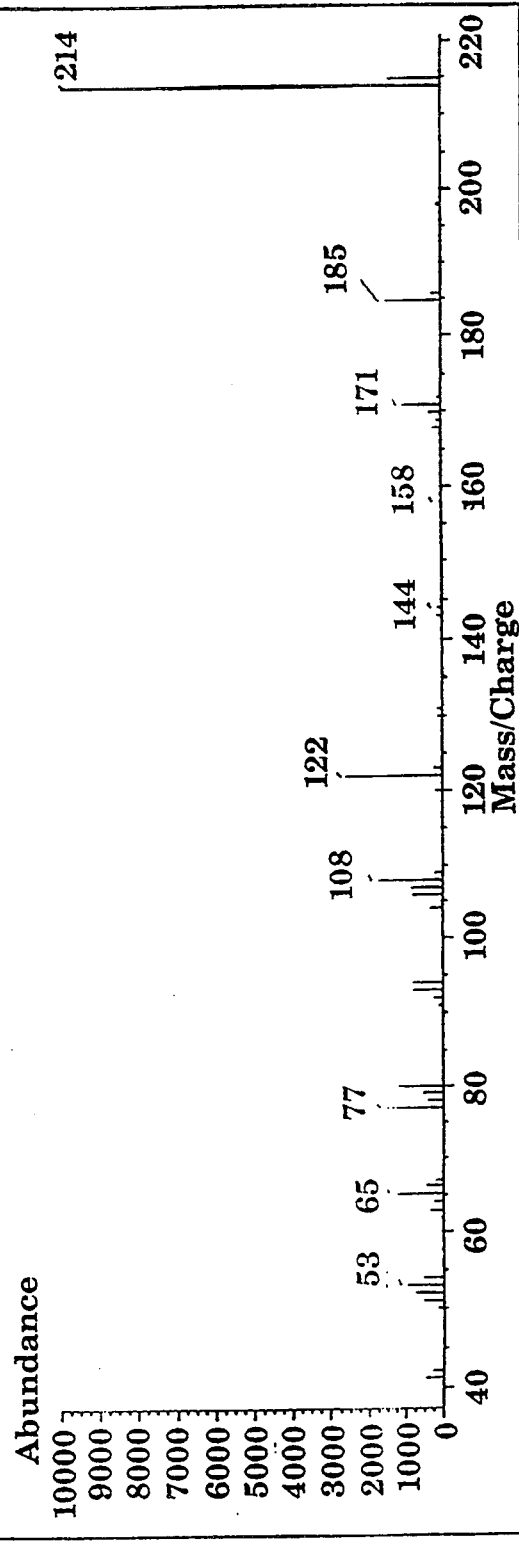
Figure 2:
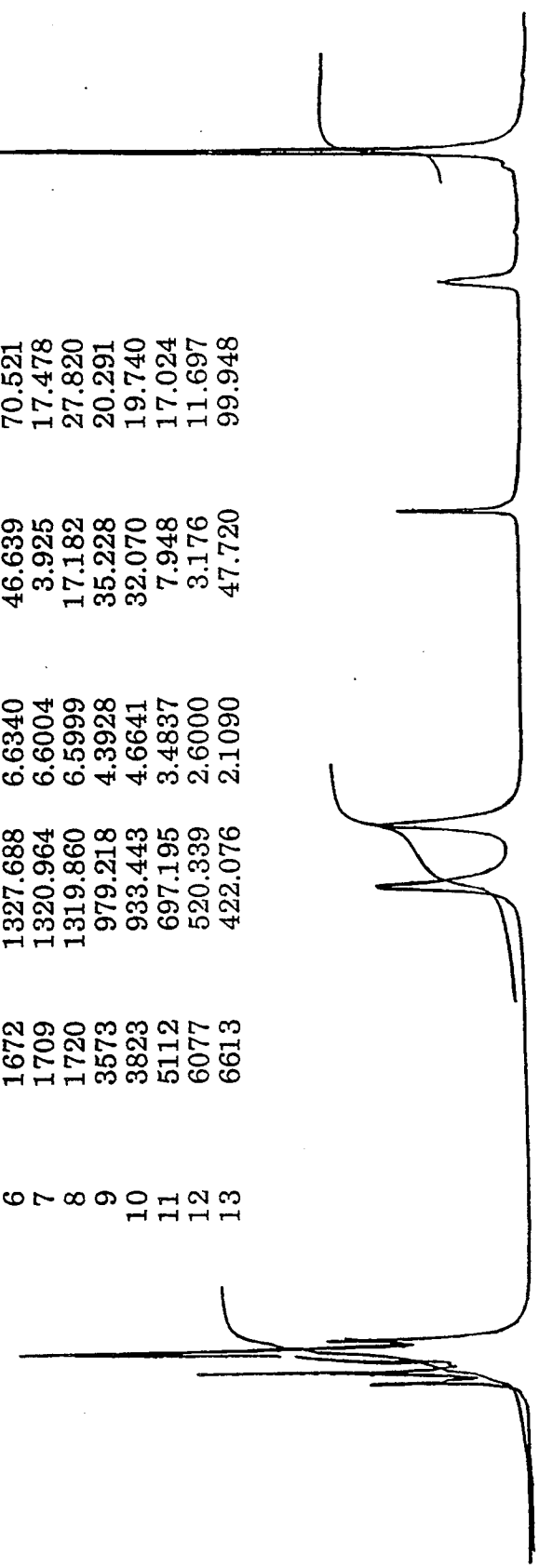
FIG. 2 is the $^1$H-NMR spectrum of DAMDPE.
Figure 3A:
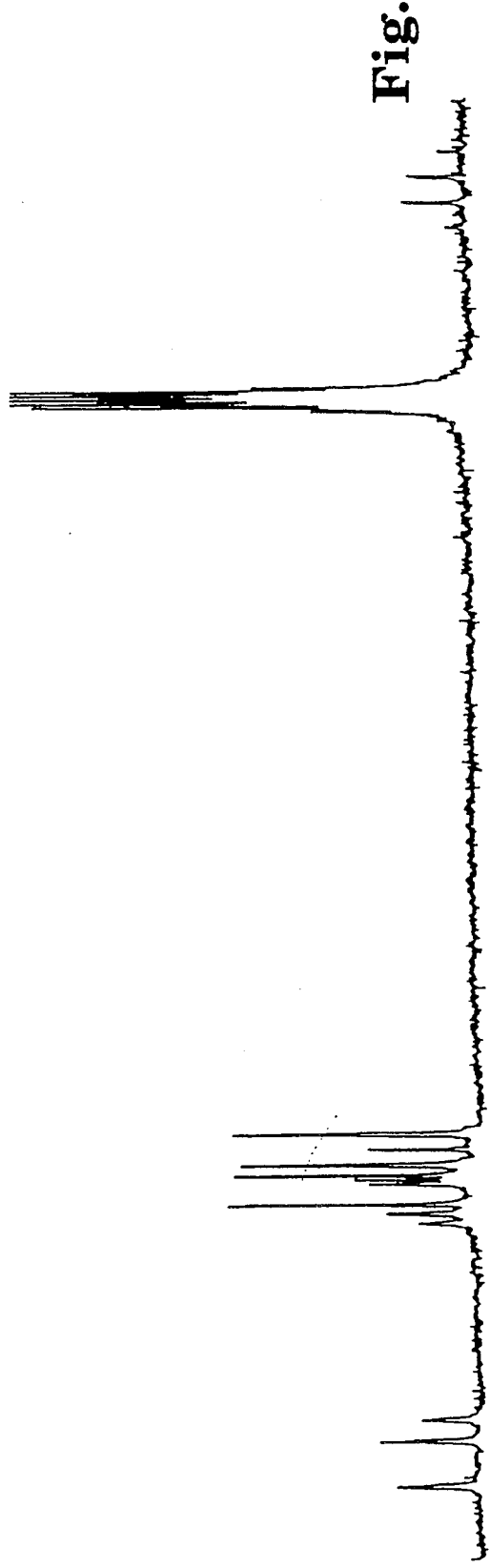
FIGS. 3(a) and 3(b) form the $^{13}$C-NMR spectrum of DAMDPE.
Figure 3B:
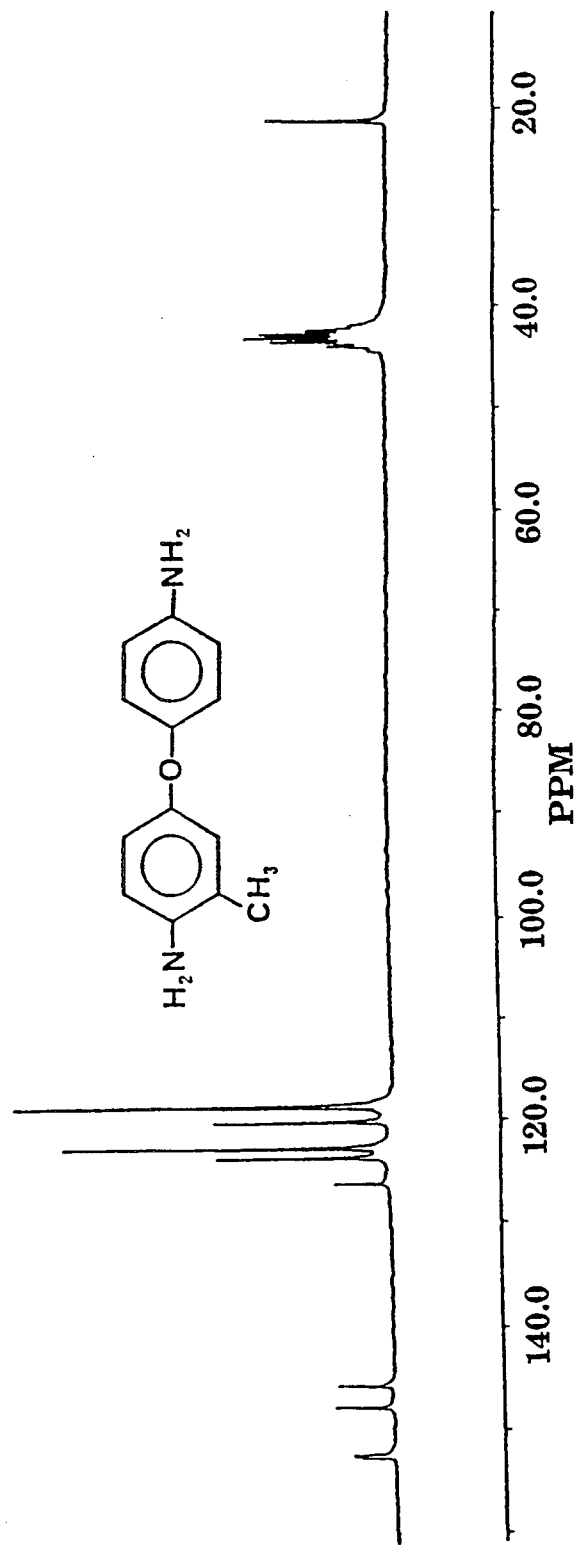
Figure 4:
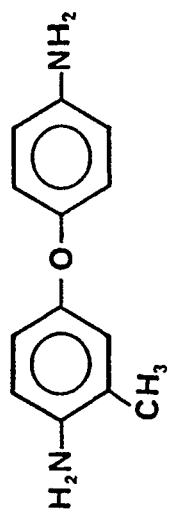
FIG. 4 is the IR spectrum of DAMDPE.
Figure 4:
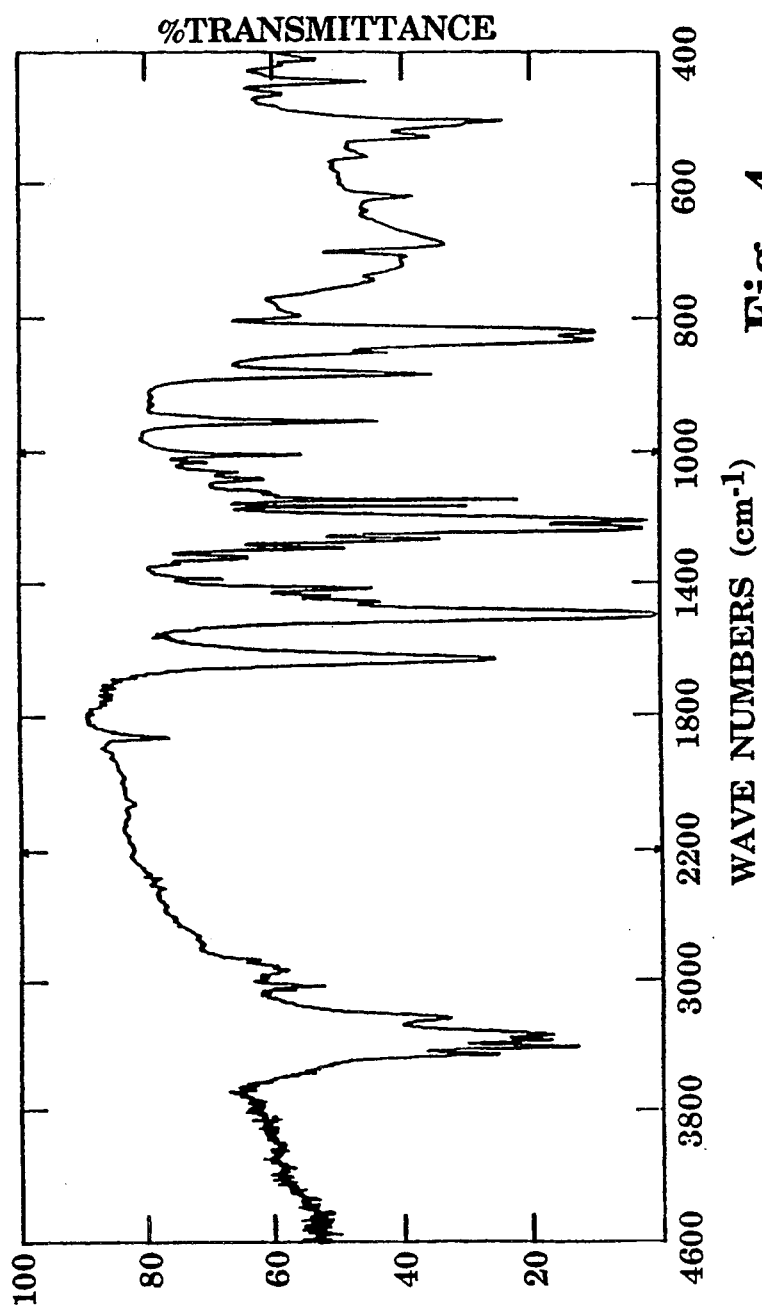

Range: 400–4600 cm$^{-1}$
Scan: 10 (every 1.0 second.)
Sample: 0.8 mg/80 mg KBr
GC gave a major peak (99.6%) at 8.11 mins retention time under the above conditions.
　The following spectra are shown in the figures:
　Mass Spectra - FIGS. 1(a) and 1(b)
　$^1$H - NMR - FIG. 2
　$^{13}$C - NMR - FIGS. 3(a) and 3(b)
　IR - FIG. 4

EXAMPLE 2

The amination was carried out as in Example 1B, but at a temperature of 240° C. Full conversion was achieved after 1.5 hours. The results were similar to those obtained in Example 1B.

EXAMPLE 3

The amination was carried out as in Example 1B, but using CuBr as the catalyst and adding gaseous ammonia intermittently to maintain the pressure. The results obtained were as in Example 1B.

EXAMPLE 4

The amination was carried out as in Example 1B, but using CuO as the catalyst. The results obtained were as in Example 1B.

EXAMPLE 5

The amination was carried out as in Example 2, but using A) CuCl and B) Cu(OAc)$_2$ as the catalysts. The results obtained in both cases were as in Example 1B.

EXAMPLE 6

Preparation of 4.4'-Diamino-2-isopropyldiphenyl Ether (DAIPE)

Into a 1 liter Parr autoclave were introduced: 4,4'-dibromo-2-isopropyldiphenyl ether (76.1 g, 0.21 moles), aqueous 25% NH$_3$ (450 ml, 5.96 moles) and CuSO$_4$·5-H$_2$O (3.6 g). The mixture was stirred at 200° C. (760–670 psi) for three hours with rapid stirring (~1200 rpm). The progress of the reaction and its completion were followed by a graph of the internal pressure of the reactor vs. time and at the end of the reaction by GC analysis and potentiometric titration of the aqueous phase for the determination of the bromide concentration.

Figure 5:
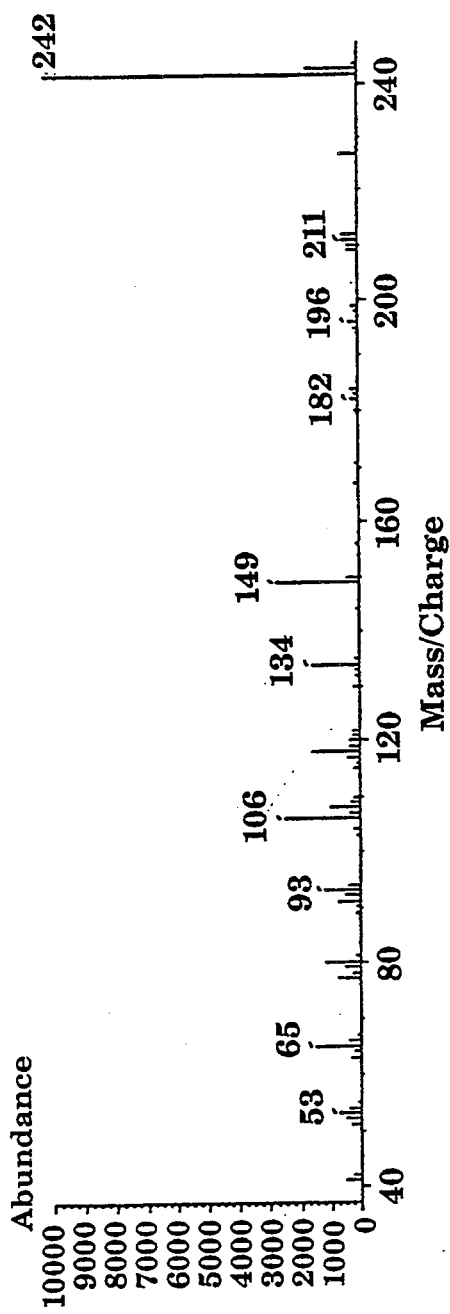
FIG. 5 is the mass spectrum of 4,4′-diamino-2-isopropyldiphenyl ether (DAIPE)

After the reaction completion, the product was extracted with CH$_2$Cl$_2$ (300 ml) and the two phases separated. The organic phase was washed with 25% aqueous NH$_3$ solution (2×50 ml) and water (2×100 ml) and the solvents were evaporated to give 44.2 g of a black oil. The aqueous phase was titrated to analyze the bromide ion concentration. The titration showed full conversion of the starting material. GCMS analysis of the crude product showed DAIPE in ca. 94% purity and 88% yield (noncalibrated GC). The impurities were identified as: isopropylphenol (1.97%), diaminodiphenyl ether (1.6%) and two monohydroxymonoamino isomers (1.45%, 1.11%). The mass spectrum and the NMR spectrum of DAIPE are shown in FIGS. 5, and 6(a) and 6(b), respectively.

EXAMPLE 7

Preparation of 1.4-Bis (4'-amino-3'-methylphenoxy) benzene

Into a 0.5 liter autoclave were placed 1,4-bis (4'-bromo-3'-methylphenoxy) benzene (16 g, 0.04 mole), aqueous 25% NH$_3$ (320 ml) and CuSO$_4$·5H$_2$O (2.3 g).

The autoclave was sealed and heated to 225° C. with rapid stirring (800 rpm). The progress of the reaction and its completion were followed by means of a graph of the internal pressure of the autoclave vs. time and, at the end of the reaction, by analysis of the Br—. After 10 hours, the autoclave was cooled to room temperature, the pressure was released and the autoclave was opened. The reaction mixture was filtered and washed with aqueous 25% NH$_3$ (50 ml) and with water (50 ml).

1,4-Bis (4'-amino-3'-methylphenoxy) benzene (8.9 g) was obtained in a purity of 85% (determined by qualitative G.C.) which, after crystallization from ethyl acetate (or acetonitrile), in the presence of active charcoal, gave a product of 99.8% purity with an m.p. of 150°–151° C.

Figure 7:
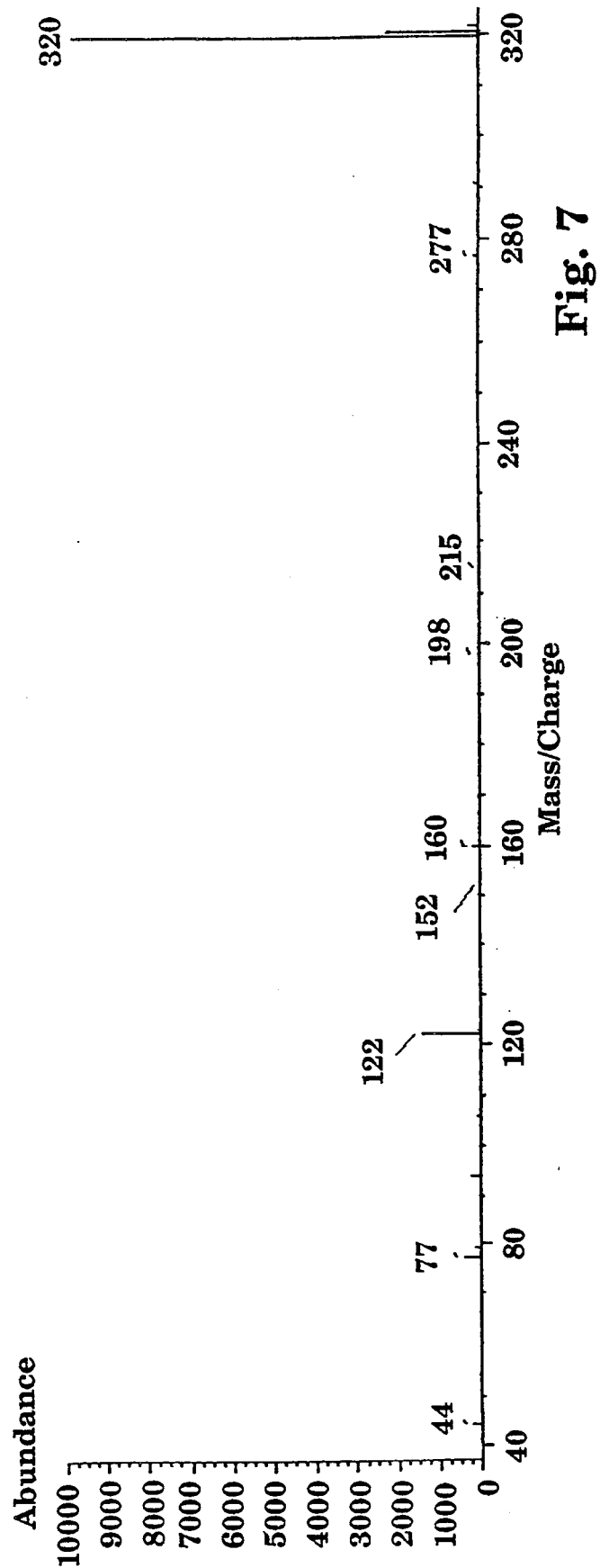
FIG. 7 is the mass spectrum of 1,4-bis (4′-amino-3′-methylphenoxy) benzene.
Figure 8:
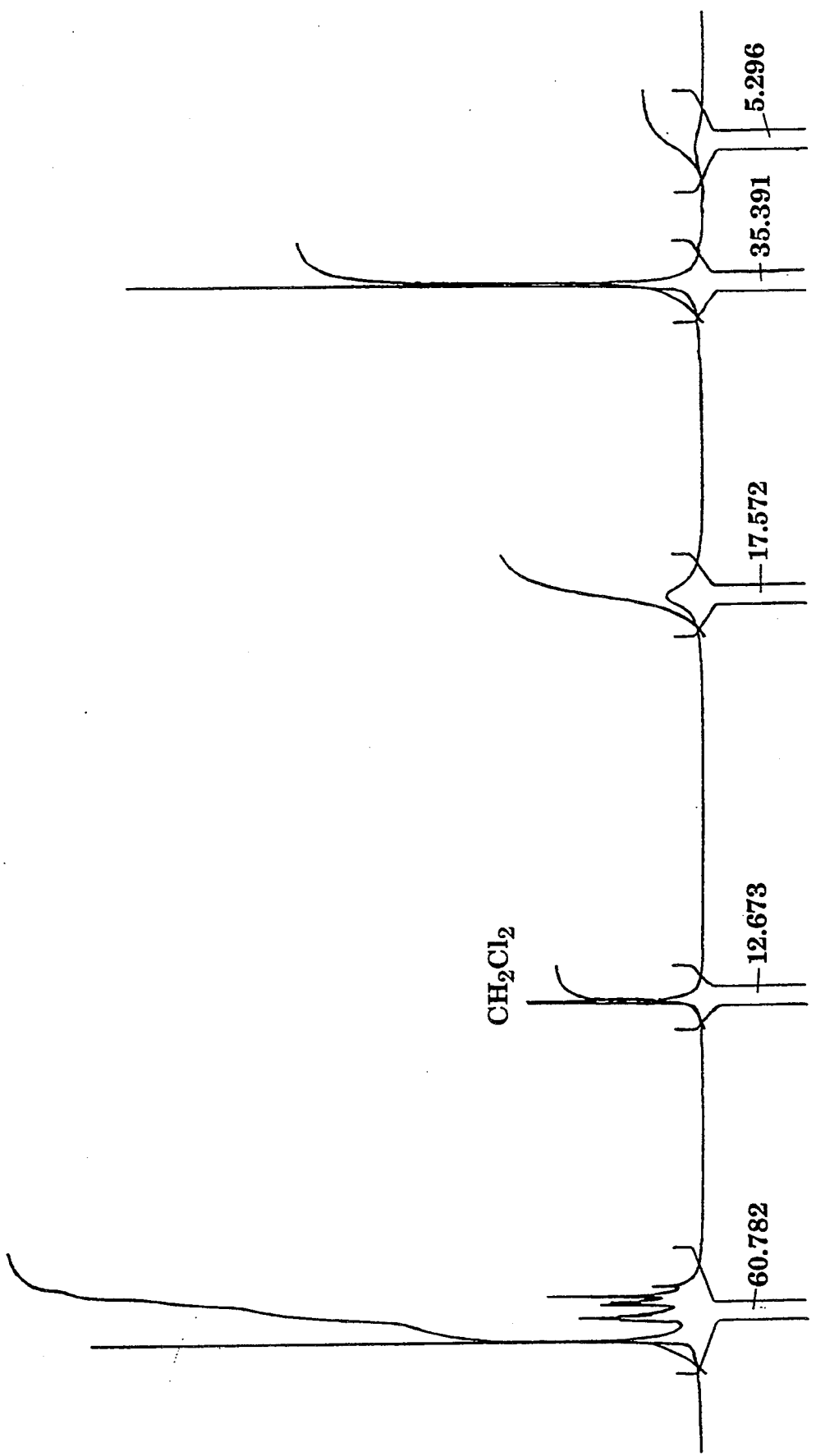
FIG. 8 is the $^1$H-NMR spectrum of 1,4-bis (4′-amino-3′-methylphenoxy) benzene in CD$_2$Cl$_2$.

The mass spectrum of the product is shown in FIG. 7, and its NMR spectrum in FIG. 8.
Elemental analysis: 74.9% C and 8.7% N.
Calc'd: 74.05% and 8.75%, respectively.

EXAMPLE 8

Preparation of 1,4-Bis (4'-amino-2'-methylphenoxy) benzene

Into a 0.5 liter autoclave were placed 1,4-bis (4'-bromo-2'-methylphenoxy) benzene (22.5 g, 0.05 mol), aqueous 25% NH$_3$ (200 ml) and CuSO$_4$·5H$_2$O (1.7 g).

The autoclave was sealed and heated to 210° C. with rapid stirring (800 rpm). The progress of the reaction and its completion were followed by means of a graph of the internal pressure of the autoclave vs. time and, at the end of the reaction, by analysis of the Br—. After 4 hours, the autoclave was cooled to room temperature, the pressure was released and the autoclave was opened. The reaction mixture was filtered and washed with aqueous 25% NH$_3$ (2×50 ml) and with water (2×200 ml).

1,4-Bis (4'-amino-2'-methylphenoxy) benzene (15.4 g) was obtained in a purity of 96.4% (determined by qualitative G.C.) which, after crystallization from ethyl acetate (or acetonitrile), in the presence of active charcoal, gave a product of 99.4% purity (determined by DSC analysis) with an m.p. of 195°–196° C.

Figure 9:
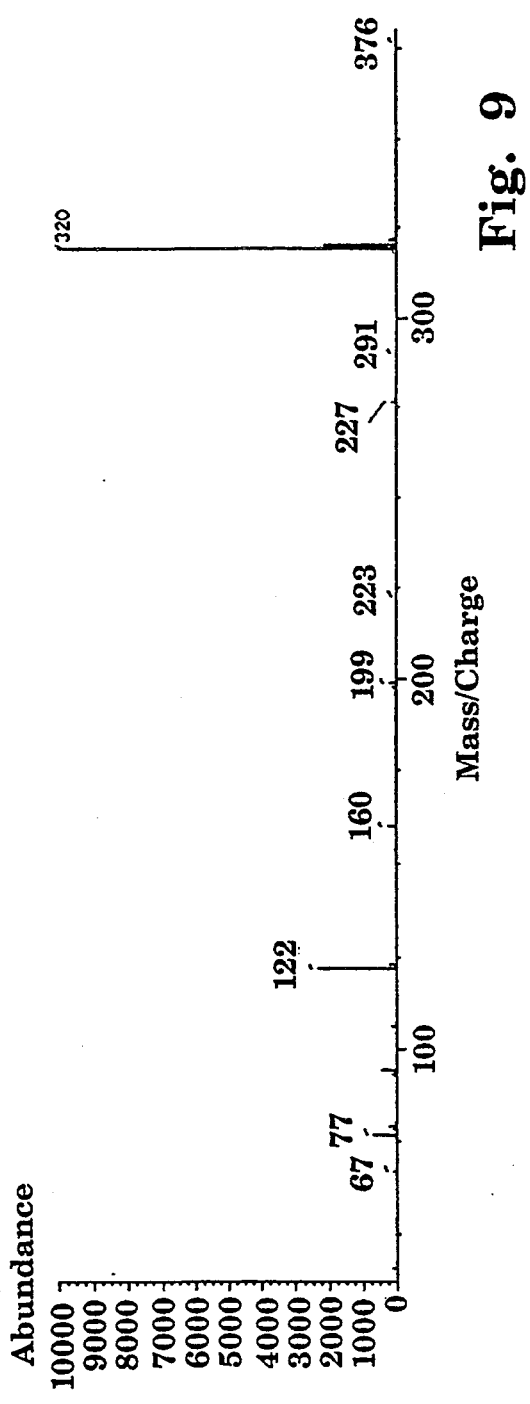
FIG. 9 is the mass spectrum of 1,4-bis (4′-amino-2′-methylphenoxy) benzene.

The mass spectrum of the product is shown in FIG. 9.
Elemental analysis: 74.9% C and 8.6% N.
Calc'd: 75.0% and 8.75%, respectively.

EXAMPLE 9

Preparation of 4.4'-Bis (4"-amino-2"-methylphenoxy) biphenyl

Into a I liter SS-316 Parr autoclave were introduced: 4,4'-bis (4"-bromo-2-methylphenoxy) biphenyl (10 g, 0.019 moles), aqueous 25% $NH_3$ (500 ml) and $CuSO_4 \cdot 5H_2O$ (0.5 g).

The autoclave was sealed and heated to 210°–220° C. (840–900 psi) for 9 hours.

After the reaction completion, the reaction mixture was filtered and washed with aqueous 25% $NH_3$ (100 ml) and hot water (150 ml).

Figure 10:
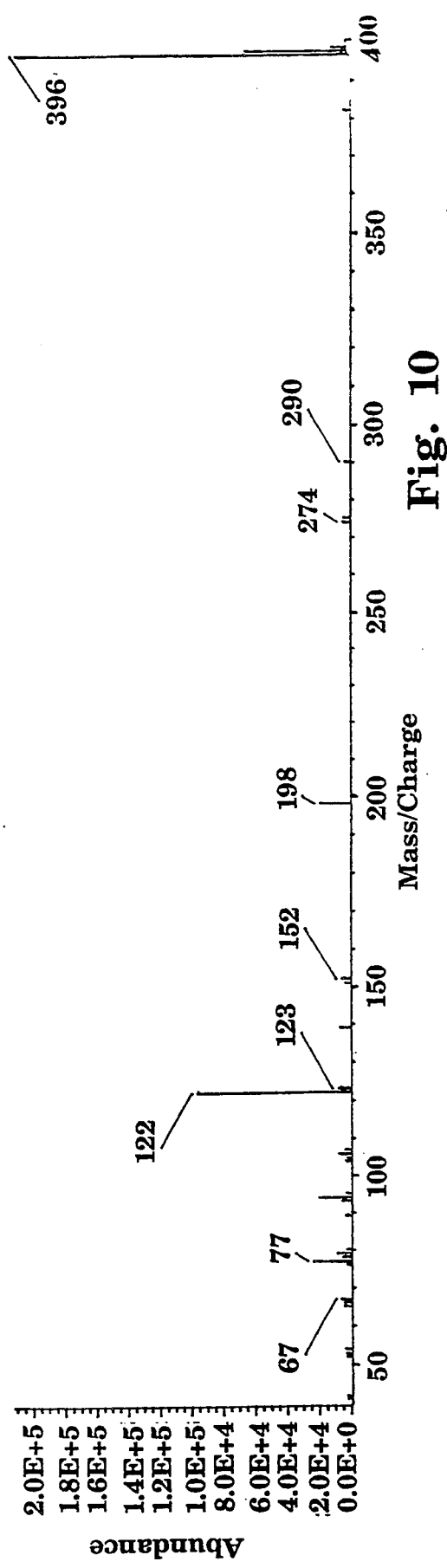
FIG. 10 is the mass spectrum of 4,4′-bis (4″-amino-2″-methylphenoxy) biphenyl.

4,4'-Bis (4"-amino-2"-methylphenoxy) biphenyl (4.5 g) was obtained with 90% purity. The mass spectrum of the product is shown in FIG. 10.

EXAMPLE 10

Preparation of 4.4'-Bis (4"-amino-2"-methylphenoxy) diphenyl Ether

Into a 1 liter SS-316 Parr autoclave were introduced: 4,4'-bis (4"-bromo-2"-methylphenoxy) diphenyl ether (10.8 g, 0.02 moles), aqueous 25% $NH_3$ (500 ml) and $CuSO_4 \cdot 5H_2O$ (0.5 g).

The autoclave was sealed and heated to 220° C. (900 psi) for 5 hours.

After the reaction completion, the reaction mixture was filtered and washed with aqueous 25% $NH_3$ (100 ml) and hot water (150 ml).

4,4'-Bis (4"-amino-2"-methylphenoxy) diphenyl Ether (6.5 g) was obtained with 93% purity (GCMS).

A recrystallized sample has the following elemental analysis: 75.6% C and 6.65% N. Calc'd: 75.7% and 6.8%, respectively.

EXAMPLE 11

4.4'-Bis (4"-amino-2"-methylphenoxy) diphenylmethane (BAMPD)

Into a 1 liter SS-316 Parr autoclave were introduced: 4,4'-bis (4"-bromo-2"-methylphenoxy) diphenylmethane (10.8 g, 0.02 moles), aqueous 25% $NH_3$ (500 ml) and $CuSO_4 \cdot 5H_2O$ (0.5 g, 2 ×$10^{-3}$ moles).

The autoclave was sealed and heated to 220° C. (900 psi) for 4 hours. After the reaction completion, the reaction mixture was filtered and washed with aqueous 25% $NH_3$ (100 ml) and hot water (150 ml). BAMPD (6.9 g) was obtained with 90% purity (GC).

A recrystallized sample has the following elemental analysis: 78.8% C and 6.7% N. Calc'd: 79.0% and 6.8%, respectively.

EXAMPLE 12

4.4'-Bis (4"-amino-2"-methylphenoxy) diphenyl sulfide (BAMPSD)

Into a 1 liter SS-316 Parr autoclave were introduced: 4,4'-bis (4"-bromo-2"-methylphenoxy) diphenyl sulfide (11.1 g, 0.02 moles), aqueous 25% $NH_3$ (500 ml) and $CuSO_4 \cdot 5H_2O$ (0.5 g, 2 ×$10^{-3}$ moles).

The autoclave was sealed and heated to 220° C. (900 psi) for 4 hours. After the reaction completion, the reaction mixture was filtered and washed with aqueous 25% $NH_3$ (100 ml) and hot water (150 ml).

BAMPSD (8.1 g) was obtained with 96% purity (GC).

Elemental analysis: 73.1% C and 6.35% N. Calc'd: 72.9% and 6.5%, respectively.

EXAMPLE 13

2.2'-Bis [4'-(4"-amino-2"-methylphenoxy) phenyl] propane (BAMPP)

Into a liter SS-316 Parr autoclave were introduced: 2,2'-bis [4'-(4"-bromo-2"-methylphenoxy) phenyl] propane (11.3 g, 0.02 moles), aqueous 25% $NH_3$ (500 ml) and $CuSO_4 \cdot 5H_2O$ (0.5 g, 2 ×$10^{-3}$ moles).

The autoclave was sealed and heated to 220° C. (900 psi) for 4 hours. After the reaction completion, the reaction mixture was filtered and washed with aqueous 25% $NH_3$ (100 ml) and hot water (150 ml).

BAMPP (8.3 g) was obtained with 92% purity (GC). A recrystallized sample has the following elemental analysis: 79.3% C and 6.2% N. Calc'd: 79.45% and 6.4%, respectively.

EXAMPLE 14

4.4'-Bis (4"-amino-2"-methylphenoxy) benzophenone (BAMPBP)

Into a 1 liter SS-316 Parr autoclave were introduced: 4,4'-bis (4"-bromo-2"-methylphenoxy) benzophenone (11 g, 0.02 moles), aqueous 25% $NH_3$ (500 ml) and $CuSO_4 \cdot 5H_2O$ (0.5 g, 2×$10^{-3}$ moles). The autoclave was sealed and heated to 220° C. (900 psi) for 4 hours. After the reaction completion, the reaction mixture was filtered and washed with aqueous 25% $NH_3$ (100 ml) and hot water (150 ml).

BAMPBP (8 g) was obtained with 93% purity (GC). A recrystallized sample has the following elemental analysis: 76.6% C and 6.45% N. Calc'd: 76.4% and 6.6%, respectively.

We claim:

1. A compound of the formula:

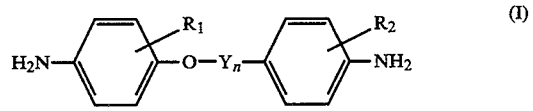

wherein:

n=0 or 1;

$R_1$ and $R_2$ are $C_1$ to $C_3$ alkyl groups and $R_2$ is also H when n=0; and Y is selected from the group

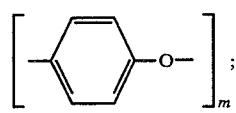

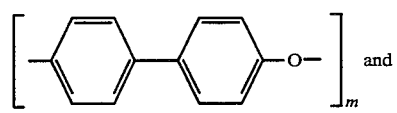 and

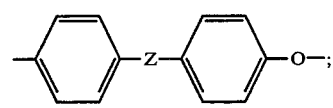

wherein:

m=1–6

Z=

CH₂ or C(CH₃)₂; with the proviso that Z is not

C(CH₃)₂ when Y is

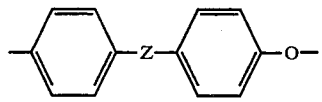

and $R_1$ and $R_2$ are each 3-methyl, and with the further proviso that when n=0 and $R_2$ is hydrogen, $R_1$ cannot be 2-methyl, 2-ethyl, 2-isopropyl or 3-methyl.

2. A compound selected from the group consisting of: 1,4-bis(4'-amino-3'-methylphenoxy) benzene, 1,4-bis(4'-amino-2'-methylphenoxy) benzene, 4,4'-bis(4"-amino-2"-methylphenoxy) biphenyl, 4,4'-bis(4"-amino-2"-methylphenoxy) diphenyl ether, 4,4'-bis(4"-amino-2"-methylphenoxy) benzophenone, 4,4'-bis(4"-amino-2'-methylphenoxy) diphenylmethane, and 2,2-bis[4'-(4"-amino-2"-methylphenoxy) phenyl] propane.

* * * * *